United States Patent [19]
Stoller

[11] Patent Number: 5,788,667
[45] Date of Patent: Aug. 4, 1998

[54] FLUID JET VITRECTOMY DEVICE AND METHOD FOR USE

[76] Inventor: Glenn Stoller, 445 E. 68th St., Apt. 9C, New York, N.Y. 10021

[21] Appl. No.: 684,400

[22] Filed: Jul. 19, 1996

[51] Int. Cl.$^6$ ............................................. A61B 17/32
[52] U.S. Cl. ........................ 604/22; 606/167; 606/170
[58] Field of Search ............................ 606/190, 167, 606/170, 159; 604/22

[56] References Cited

U.S. PATENT DOCUMENTS

| | | | |
|---|---|---|---|
| 4,678,459 | 7/1987 | Onik et al. | 604/22 |
| 5,037,432 | 8/1991 | Molinari | 606/167 X |
| 5,496,267 | 3/1996 | Drasler et al. | 606/159 X |
| 5,562,692 | 10/1996 | Bair | 606/167 |
| 5,571,126 | 11/1996 | Dorsey | 606/190 X |
| 5,591,184 | 1/1997 | McDonnell et al. | 606/167 |
| 5,620,414 | 4/1997 | Campbell, Jr. | 606/167 X |

FOREIGN PATENT DOCUMENTS

| | | | |
|---|---|---|---|
| 4332549 | 11/1992 | Japan | 606/167 |
| 6090957 | 4/1994 | Japan | 606/167 |
| 8906113 | 7/1989 | WIPO | 606/167 |
| 9428807 | 12/1994 | WIPO | 606/167 |

*Primary Examiner*—Michael H. Thaler
*Attorney, Agent, or Firm*—Notaro & Michalos P.C.

[57] ABSTRACT

A fluid jet cutter for removing tissues from a patient's body, and in particular for performing vitrectomy surgery within the patient's eye, is provided having an elongated casing tube connected to a handle at a proximal end, a water supply tube through the casing tube interior, and an opening through the side of the casing tube adjacent a distal end. The distal end of the tube is sealed closed with a hemispherical cap. A nozzle is attached to the distal end of the water supply tube and located adjacent the proximal side of the opening in the casing tube. A vacuum is provided inside the casing tube around the water supply tube. The other end of the water supply tube is connected to a pressurized water supply adjacent the handle. The nozzle forms the pressurized water into a jet which can cut tissues. The vacuum both draws tissues into the interior of the casing tube through the opening, into the path of the water jet for cutting and/or disintegration, and aspirates the cut tissues. All of the cutting action of this water jet cutter is within the confines of the casing tube; any water supplied through the water supply tube for the water jet either impinges on the hemispherical cap and is withdrawn by the vacuum, or cuts tissue within the casing tube and is withdrawn by the vacuum with the cut tissue. The vacuum can be regulated by the user to prevent excess suction from occurring at the opening which would cause additional stresses on the patient's healthy tissues. In a second embodiment, the water jet vitrectomy cutter has three distinct passages through the casing tube interior, rather than two, for adding a second vacuum. Other embodiments of the cutter and methods for the use of the cutters of the invention are also provided.

49 Claims, 9 Drawing Sheets

FLUID JET VITRECTOMY DEVICE AND METHOD FOR USE

FIELD AND BACKGROUND OF THE INVENTION

A submission by an inventor of this invention to the Document Disclosure Program was made on Jul. 6, 1995, having been assigned document number 388835, and which is hereby incorporated by reference.

The present invention relates, in general, to the field of fluid jet surgical cutting, and more particularly, to a micro-surgical cutting device for cutting and removing vitreous or other undesirable tissues from a patient's eye.

Vitreous is a clear, jelly-like substance found in the posterior segment of the human eye behind the lens of the eye. While vitreous appears to be a simple gelatinous substance, it actually contains many collagen fibers linking it to the retina of the eye.

It is sometimes necessary to remove vitreous from a patient's eye to improve the patient's vision. The presence of the collagen fibers prevent a method of vitreous removal in which the vitreous is simply pulled from the eye cavity by suction. Doing so would severely damage the eye by tearing the retina.

Thus, vitreous must be cut or disintegrated before it can be safely removed from a patient's eye without causing harm and damage to the eye.

Hand held vitrectomy cutters are known for use in ocular surgery. A popular type of cutter is the O'Malley Ocutome, which uses a guillotine effect of an oscillating inner tube with a sharpened end moving past an opening in a close-fitting outer tube to cut the vitreous. A vacuum is generated at the opening in the outer tube to pull some of the vitreous to be cut into the path of the sharp end of the oscillating inner tube, which slices the vitreous. The vitreous is aspirated from the eye cavity by the vacuum, and then transported through tubes inside the cutter handpiece to a waste storage receptacle.

U.S. Pat. No. 3,776,238 discloses another conventional guillotine-type vitreous cutter including vacuum removal of cut tissue in conjunction with a fluid supply. The device uses a mechanical cutter, like the O'Malley Ocutome, to separate the vitreous, which is then removed through the vacuum tube. It has a fluid supply for replacing the vitreous removed by the cutter.

Guillotine-type vitrectomy cutters experience fluctuations in the strength of the vacuum applied to the vitreous as a result of the motion of the inner tube sliding back and forth over the orifice of the outer tube thereby causing the patency of the orifice of the outer tube to constantly change from fully blocked to fully patent.

The fluctuation in the patency of the orifice in turn causes what is referred to as "vitreous turbulence", or pulsatile vitreous flow, whereby the vitreous and tissues it is still attached to pulsate at a frequency which is related to that of the oscillating inner tube, as the vitreous is alternately jerked inside the outer tube by a strong vacuum, and released as the inner tube slides over the opening and closes it, cutting the vitreous and sealing off the vacuum.

Pulsatile vitreous flow can create traction on the retina leading to the formation of retinal breaks and/or bleeding. Further, cutting near the surface of the retina becomes dangerous as the retina or other structures can suddenly and unexpectably jump into the orifice and be cut.

Other problems associated with guillotine-type cutters include lack of ability of the cutter to continuously cut tissue since the slicing motion of the inner tube only cuts in one direction leading to decreased efficiency of vitreous removal, difficulty in creating curved vitrectomy cutters, difficulty in decreasing the diameters of the cutter tubes to minimize the intrusion into the patient's body, and dulling of the sharpened end of the inner rod during surgery.

U.S. Pat. No. 3,930,505 discloses a hand held cutter which directs a fluid jet at tissue, such as the lens of the eye, to disintegrate and pulverize the material. The fluid jet supply is located inside surrounding tubes, but the fluid jet is directed perpendicular to the surrounding tube through a beveled opening to a point outside the surrounding tubes for impinging directly on the material to be cut. The disintegrating and cutting action occurs entirely outside of the surrounding tubes. The disintegrated material is then aspirated into a vacuum tube located adjacent the fluid jet supply to a waste storage container.

U.S. Pat. No. 5,322,504, discloses a similar fluid jet cutter having a cannula, formed by two concentric tubes, used to supply a fluid jet and also to suction away emulsified lens material. The fluid jet is provided through the inner concentric tube, while the aspirating vacuum is provided in the annulus between the inner and the outer tube. The fluid jet is directed parallel with the cannula out the end of the inner tube and the disintegration and cutting all take place outside of the cannula tubes. This cutter uses the vacuum only for evacuation for the emulsified or disintegrated material and not for bringing the material to be cut into the path of the water jet.

These fluid jet cutters make no provision for protecting adjacent regions of the eye which are not intended to be disintegrated by the fluid jet, as the fluid projects directly from the tips of the cutters onto the offending material. Other, healthy tissues adjacent the material being removed may be unintentionally subjected to the destructive effects of the fluid jet.

Fluid jet cutters are known for use in other areas of surgery, as shown by U.S. Pat. No. 5,496,267, which discloses an atherectomy fluid jet cutter. The atherectomy cutter has a catheter with a large opening in the side wall and it is positioned within a vessel by a balloon. A fluid jet is oriented parallel within the catheter and directed toward an end wall of the catheter. An evacuation port is provided in the catheter end wall for removing cut tissue. The catheter opening is positioned around the plaque deposit and the fluid jet is directed onto the surface of a stationary plaque deposit, thereby disintegrating it. The material is then removed through the evacuation port. Several embodiments having guide lumens within the catheter are also taught. This cutter is disclosed for use within human blood vessels, as opposed to the human eye and again only uses the vacuum for removal of the ablated or disintegrated material, and not to bring material to be cut into the path of the fluid jet.

SUMMARY OF THE INVENTION

The fluid jet cutter of the present invention overcomes many of the problems associated with known vitrectomy cutters and is directed to fluid jet cutters for cutting and removing tissue that can be adapted for different types of surgeries, beyond those performed within the eye.

In accordance with the invention, a surgical fluid jet cutter for use inside a patient's body is provided having an elongated casing tube connected to a handle at a proximal end, a fluid supply tube through the casing tube interior, and an opening through the side of the casing tube adjacent a distal end. The distal end of the casing tube is sealed closed with a hemispherical cap. A nozzle is attached to the distal end of the fluid supply tube and located adjacent the proximal side of the opening in the casing tube. A vacuum is provided inside the casing tube around the fluid supply tube. The other end of the water supply tube is connected to a pressurized water supply adjacent the handle.

The nozzle forms the pressurized fluid into a jet which can cut tissues. The nozzle may be unitarily formed with the fluid supply tube. The vacuum both draws tissues into the interior of the casing tube through the opening, into the path of the fluid jet for cutting and/or disintegration, and removes the cut tissues and fluid jet effluent from the casing tube. All of the cutting action of this fluid jet cutter is within the confines of the casing tube; any fluid supplied through the fluid supply tube for the fluid jet either impinges on the hemispherical cap and is withdrawn by the vacuum, or cuts tissue within the casing tube and is withdrawn by the vacuum with the cut tissue. The vacuum can be regulated by the user or electronically to create optimal conditions for precise and safe cutting.

In a second embodiment, the fluid jet vitrectomy cutter has three distinct passages through the casing tube interior, rather than two. The three passages are for the fluid jet supply, a low vacuum and a high vacuum. The distal end of the casing tube is again sealed closed by a hemispherical cap.

The fluid jet supply passage is a narrower elongated tube located proximately to the casing tube interior wall with the nozzle at one end. The nozzle is again located adjacent the opening in the casing tube, and oriented such that the pressurized fluid forced through the nozzle will form a thin jet across the opening, directed at the hemispherical cap.

The low vacuum passage is an elongated tube oriented concentrically within the casing tube. The low vacuum tube has an aspiration opening in its side aligned with the casing opening and the nozzle. The distal end of the low vacuum tube is closed, while the handle end is connected to a low vacuum. The low vacuum is for suctioning tissues into the path of the fluid jet within casing tube for cutting and for removing cut tissues from the cutter to a separate waste container.

The remaining volume within the casing tube defines the high vacuum passage. A high vacuum is connected to the high vacuum passage in the handle of the cutter. The high vacuum is for evacuating the fluid from the fluid jet and any cut tissue which is entrained in its path from within the cutter hand piece. A waste container is connected to both the high and low vacuum passages for storing the aspirated materials until they can be properly disposed of.

A third embodiment is provided in which the fluid supply tube and nozzle are caused to rotate. This embodiment can be used with the structure of either of the previous embodiments. The rotation is caused by the pressurized fluid being forced through a turbine connected to the fluid supply tube. A bearing connection allows the distal end and nozzle of the fluid supply tube to rotate, while the proximal end, connected to the source of pressurized fluid remains stationary. The rotating fluid jet created by the apparatus of this embodiment is believed to have additional beneficial cutting properties. The fluid supply tube and nozzle can also be rotated using electric motor means or by other known mechanical means. Additionally, a rotational motion could be imparted to the fluid within the fluid supply tube using a static turbine to swirl the fluid through the fluid supply tube.

In each of the embodiments described, the nozzle can have different spray openings for forming various shaped fluid jets. Possible configurations for the spray openings include a single circular or beveled opening, multiple circular or beveled openings arranged in triangular, rectangular, circular or X-shaped patterns. Other patterns are also envisioned. Alternatively, the fluid jet passage could be provided with multiple nozzles.

In each of the embodiments described, the fluid jet may be a continuous stream or a pulsed stream.

The vacuums and pressurized fluid source may be created by any known means. The pressurized fluid can be generated by a known type of pump such as a positive displacement pump, located either within the handpiece of the cutter or in an attached console unit. One such apparatus provided has a driving beveled gear which is powered by a motive force, linked to a driven beveled gear, which translates the rotational motion through a seal to a pump, which accelerates and pressurizes fluid passing through the pump. The pump may be a simple gear pump, in which two gears are linked, one gear being driven by the driven beveled gear. The rotational motion of the gears and gear teeth accelerate and pressurize the fluid to a desired level.

A control console for the cutter is also provided having a software driven control system, at least one vacuum source and differential control of the vacuum strength, a waste storage receptacle, a fluid pressure source, a fluid jet pulse former, a pressure regulator, a reflux regulator, and a foot control switch to allow the physician to keep his hands free for conducting the surgery with the cutter. The vacuum source may be created by any known source including a venturi, diaphragm or peristaltic pump. Further the fluid pressure source may be contained within the hand piece and controlled by the control system.

In operation, the vitrectomy cutter is inserted within a patient's eye. The casing tube opening is located within or next to the vitreous to be removed, and the vitreous is aspirated through the opening into the path of the pressurized fluid jet spray. The fluid jet spray is fine and at sufficient pressure to cut through vitreous matter. The emulsified vitreous is replaced by a suitable sterile, physiologic solution via an infusion cannula sewn to the surface of the eye.

In the first embodiment, the single vacuum both draws vitreous or other tissue to be cut, such as lens fragments, into the casing tube, and withdraws the cut and disintegrated material and the fluid from the fluid jet cutting tool. The vacuum flow rate and the fluid jet flow rate are monitored by electronic sensors in the control unit such that the vacuum flow is always at least equal, and usually in excess of that required to remove the jet effluent. The amount of excess vacuum flow is controlled by the surgeon and is used to aspirate tissue into the orifice of the outer casing, thereby determining the rate at which tissue enters the cutter. These features ensure that material is never accidently expelled from the outer casing orifice and further that low flow cutting can take place despite the present of a higher flow fluid jet.

In the three passage embodiment, the high vacuum within the casing withdraws the relatively high flow of effluent from the fluid jet which reverses direction after impacting the hemispherical cap at the distal end of the tube, through the casing tube, to a disposal unit. The low vacuum created within the low vacuum passage serves to both aspirate material through the outer casing orifice into the path of the fluid jet and to also remove the cut tissue from the cutter hand piece. The flow rate of the low vacuum determines the rate at which tissue enters the cutter. The high vacuum flow rate is matched via electronic sensors to the fluid jet flow rate such that the two flow rates are nearly equal, thereby negating the effect of the high vacuum suction on the rate at which tissue enters the outer casing orifice for cutting. The three passage embodiment allows for greater independence between the flow of the fluid jet and the rate at which tissue enters the cutter orifice. This allows a relatively low tissue aspirating suction flow to exist in the presence of the higher vacuum suction needed to evacuate the effluent of the fluid jet. The electronic control system prevents the fluid jet from over whelming the high vacuum so that material is never accidently expelled through the orifice of the outer casing.

The fluid jet may be pulsed at frequencies selected by the surgeon using the control panel or operated continuously. The fluid jet cutter functions with an orifice which is continuously and equally open at all time during operation and with a non-fluctuating aspirating vacuum force continuously present at the outer casing orifice. These features allow for continuous and non-pulsatile flow of tissue into the cutter hand piece.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENTS

Figure 1:
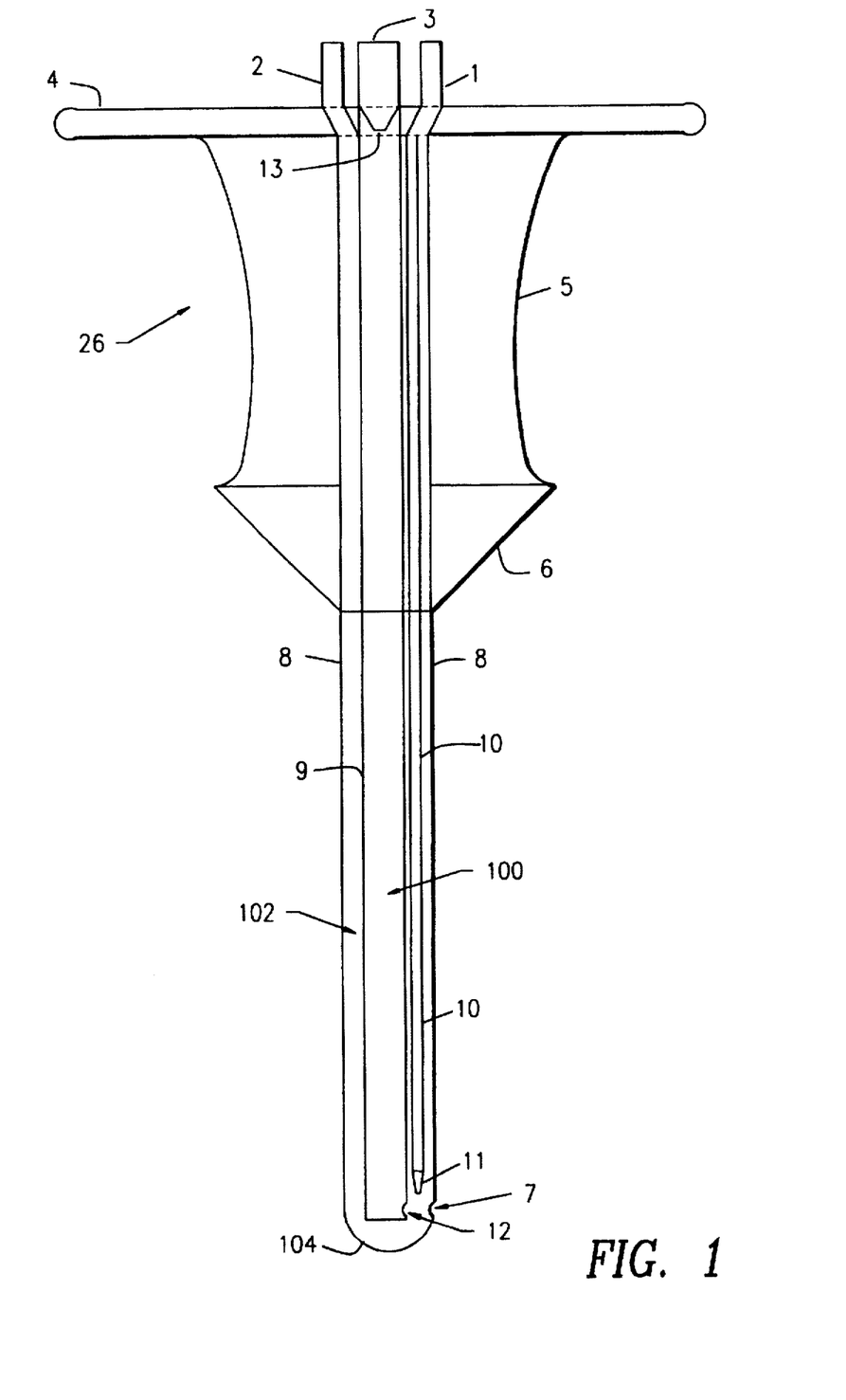
FIG. 1 is a sectional view of a cutter handpiece of the present invention.

Referring to the drawings, in which like reference numerals are used to indicate the same or similar elements, FIG. 1 shows a cutter handpiece 26 having a grip 5 surrounding an outer casing tube 8. The grip 5 is sculpted to comfortably fit a person's hand, and has flange 4 at its base and crown 6 tapering toward the exposed end of casing tube 8. Casing tube 8 extends from flange 4 through the grip 5 and contains the working elements of the cutter handpiece 26. The proximal end of casing tube 8, adjacent flange 4 is sealed closed.

Figure 3:
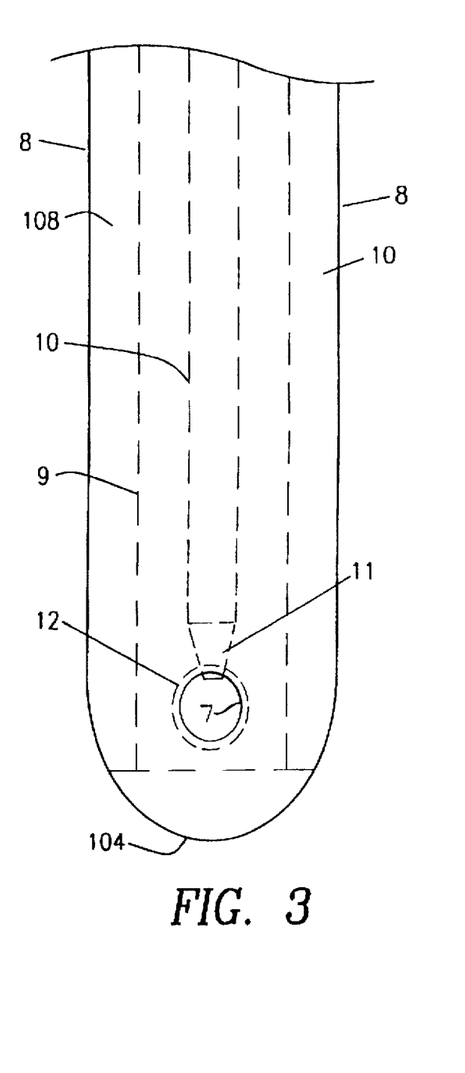
FIG. 3 is a front elevation of the cutting tip of the cutter of the present invention as shown in FIG. 2.

The casing tube 8 has an opening, or orifice 7 adjacent the distal end, farthest from the crown 6, as best shown in FIG. 3. The orifice 7 is slightly oval in shape. A hemispherical end cap 104 closes the distal end of the casing tube 8 and provides a rounded tip to the cutter handpiece 26.

In the embodiment of the cutter handpiece 26 shown in FIG. 1, three distinct passages are present inside the casing tube 8. The first passage is defined by fluid supply tube 10, located adjacent the inside of casing tube 8. Fluid supply tube 10 is an elongated tube inside casing tube 8, and is positioned so that one end is near the orifice 7 in the casing tube 8. A nozzle 11 is attached to the end of tube 10 adjacent the side of the orifice 7 and directed across the orifice 7 at the hemispherical cap 104 of the casing tube 8. A fluid supply port 1 is used to connect fluid supply tube 10 to a fluid source (not shown in FIG. 1). Preferably, flexible tubing of any known type can be used to make this and other connections where a rigid connection would not be required.

The second, low vacuum, passage 100 is located within low vacuum tube 9. Low vacuum tube 9 is an elongated tube oriented concentric with the casing tube 8, and closed at a distal end near the hemispherical cap 104. Low vacuum tube 9 has an aspiration port 12 at the distal end which is aligned with casing tube orifice 7. The fluid supply tube 10 is located in the annulus formed between the low vacuum tube 9 and the interior wall of casing tube 8. A low vacuum port 3 is connected to the proximal end of the low vacuum tube 9 within the grip 5 for connecting to a low vacuum source (not shown in FIG. 1) through the proximal end of casing tube 8 and flange 4. A variable attenuator 13 may be placed either within low vacuum tube 9, or low vacuum port 3, to control the strength of a vacuum provided in low vacuum passage 100.

The third, high vacuum, passage 102 is defined by the casing tube 8, and the volume not occupied by either the low vacuum tube 9 or the fluid supply tube 10. A high vacuum connecting port 2 is provided through the flange 4 of the grip and sealed end of casing tube 8 to connect the casing tube 8 with a high vacuum source (not shown in FIG. 1).

Figure 2:
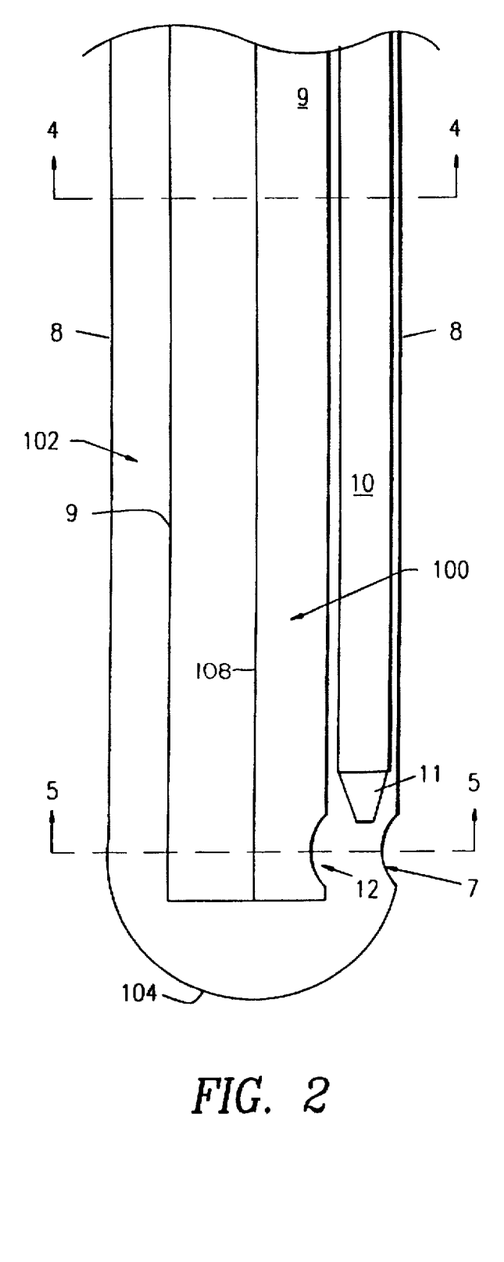
FIG. 2 is a sectional view of the cutting tip of a different embodiment of cutter of the present invention.

FIGS. 2 and 3 show the distal end of the casing tube 8 of an alternate embodiment of the cutter in more detail. The orifice 7 is seen to align with aspiration port 12, while nozzle 11 is adjacent the proximal side of each opening 7, 12.

Figure 4:
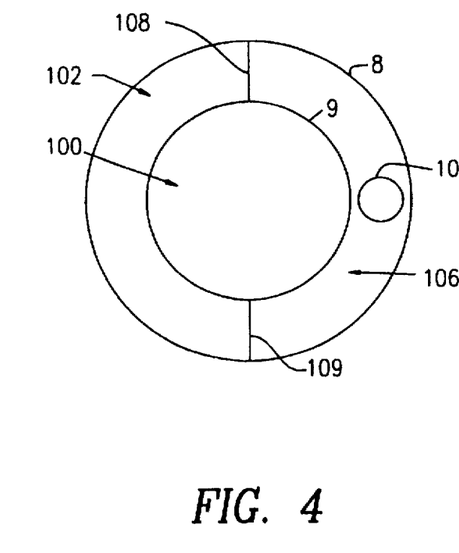
FIG. 4 is a sectional view taken along line 4—4 of FIG. 2.
Figure 5:
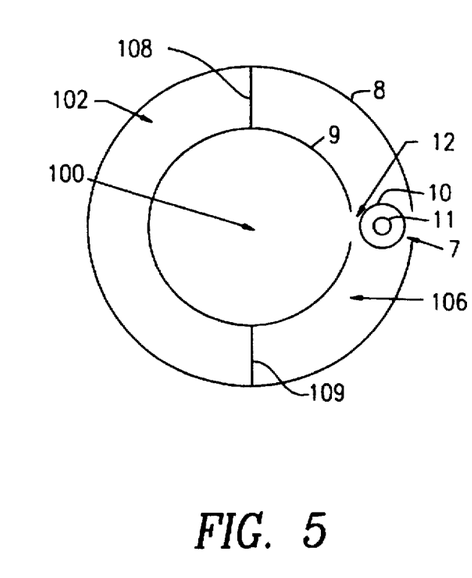
FIG. 5 is a sectional view taken along line 5—5 of FIG. 2.

An optional divider 108 is used to section the high vacuum passageway 102, and decrease its size. The divider 108 extends between the low vacuum tube and the inside wall of casing tube 8 all along the length of low vacuum tube 9 between the aspiration port 12 and flange 4. As seen in FIGS. 4 and 5, a second optional divider 109 is similarly located on the opposite side of the low vacuum tube 9. The dividers 108, 109 create a region 106 in which the vacuum does not act, or has minimal effect. The divider 108, 109 may be positioned at various points around the circumference of the low vacuum tube 9, provided orifice 7 and aspiration port 12 are not blocked. Alternately, a single divider extending from opposite interior walls of the casing tube 8 and positioned appropriately could be used.

In FIGS. 4 and 5, the sectional views of the casing tube 8 show the relationship of the fluid supply tube 10 and low vacuum tube 9 and the high vacuum passage 102. Low vacuum passage 100 is shown inside low vacuum tube 9, with aspiration port 12 aligned with orifice 7.

When a cutter 26 according to this embodiment is operated, fluid is supplied under high pressure to the fluid supply tube 10, and directed by nozzle 11 to form a fluid jet (not shown) that impinges on hemispherical cap 104. The fluid jet is thin and powerful and can effectively cut or disintegrate human and animal tissues.

When the cutter 26 is inserted within a patient's body, as for example, into an eye, a vacuum of low strength is provided through low vacuum passage 100 within low vacuum tube 9. The low vacuum is present at aspiration port 12, and is used to suction tissue or material to be cut through orifice 7, and into the path of the fluid jet emitted from nozzle 11. The material is cut and then aspirated through low vacuum tube 9. Fluid not aspirated with the cut material is removed from the casing tube 8 by a higher strength vacuum provided in high vacuum passage 102. The two vacuum suction flow rates and fluid jet flow rate are monitored and regulated by any known electronic means in the console unit (not shown) to prevent cut tissue and effluent from exiting the casing tube 8 and to aspirate tissues through orifice 7 at an appropriate rate.

Figure 6:
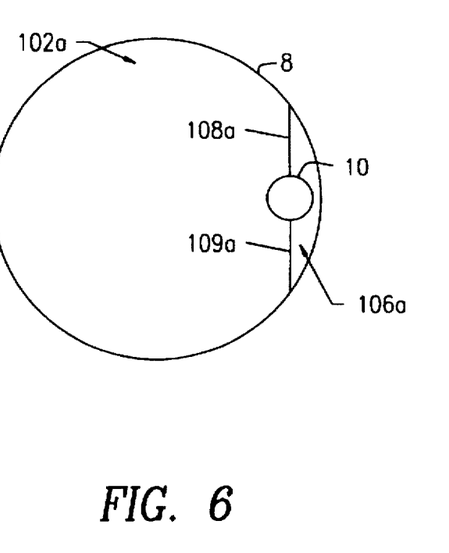
FIG. 6 is a sectional view taken along line 6—6 of FIG. 8.
Figure 7:
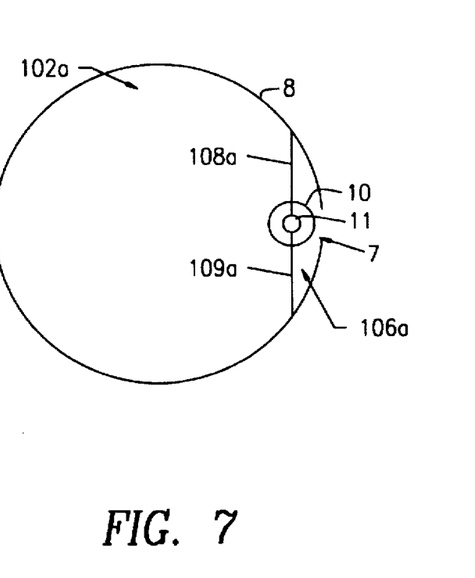
FIG. 7 is a sectional view taken along line 7—7 of FIG. 8.
Figure 8:
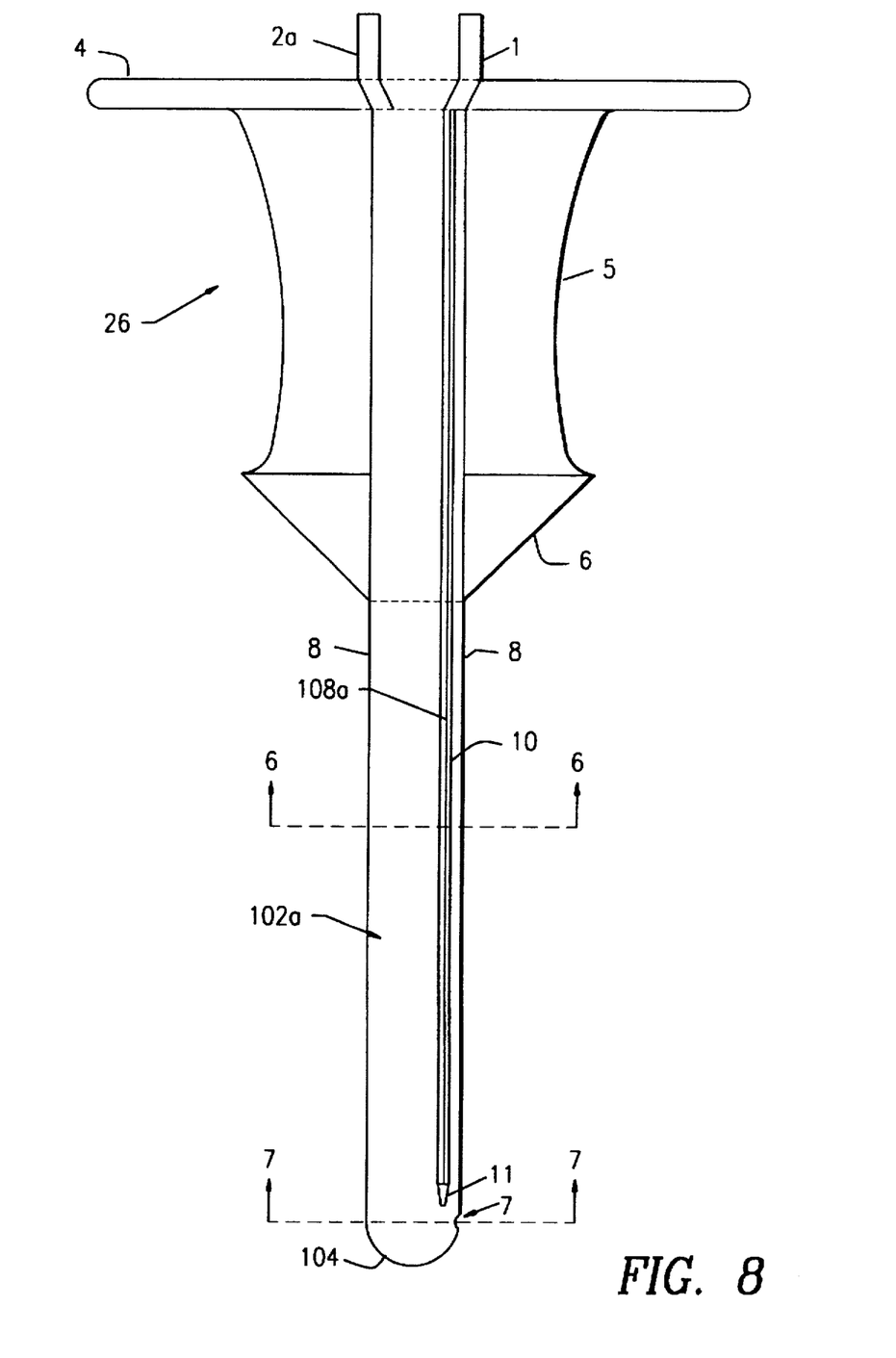
FIG. 8 is a sectional view of another embodiment of the cutter handpiece.
Figure 9A:
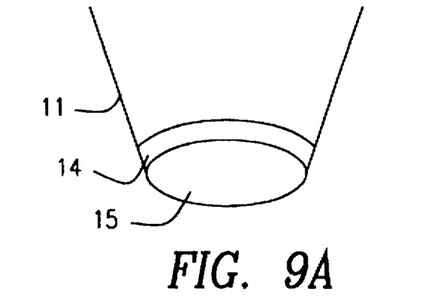
FIGS. 9A–9B are front perspective views of different embodiments of nozzle tips for use with the present invention.
Figure 9B:
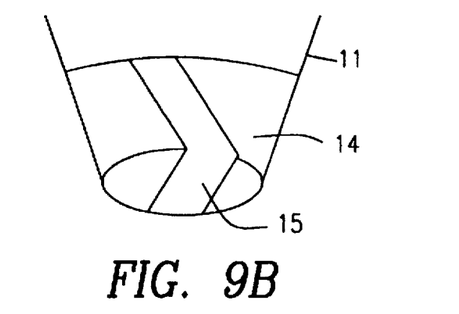
Figure 10A:
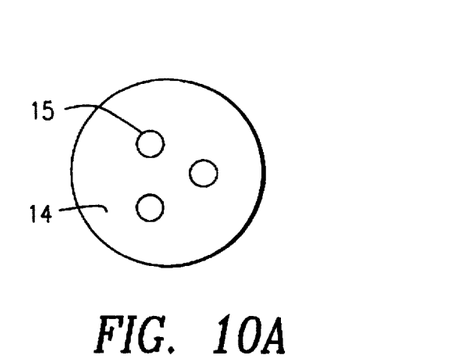
FIGS. 10A–10D are bottom plan views of further embodiments for nozzle tips for use with the cutter of the present invention.
Figure 10B:
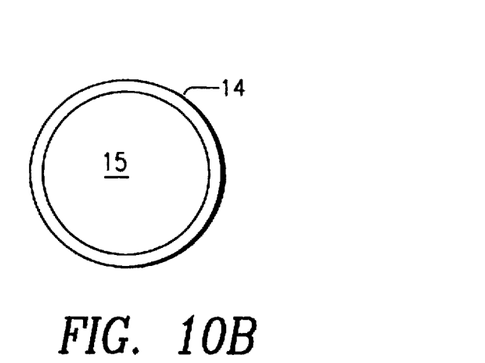
Figure 10C:
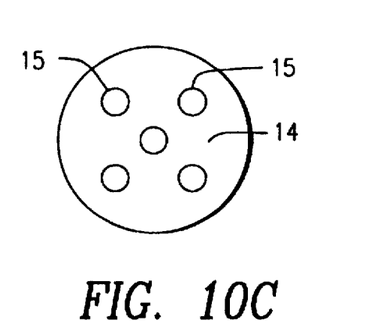
Figure 10D:
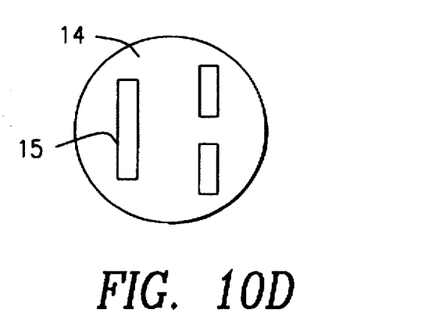

FIG. 8 shows an embodiment of the cutter 26 in which only one vacuum is provided within the casing tube 8, through vacuum port 2a in flange 4 of the grip 5. The vacuum surrounds the fluid supply tube 10 in vacuum chamber 102a within casing tube 8. The vacuum suction flow rate and fluid jet flow rate are monitored and regulated by any known electronic means in the console unit. The vacuum flow rate is at a level which will both effectively evacuate the effluent from the fluid jet, preventing the accidental expulsion of cut tissue and fluid from within casing 8 through orifice 7 back into the patient's body, and also cause tissue to be aspirated into orifice 7 at an appropriate rate. In this embodiment, an optional divider 108A is oriented on one side of fluid jet supply tube 10 and as shown in FIGS. 6 and 7, a second optional divider 109A is oriented on the opposite side of fluid jet supply tube 10. The dividers 108A, 109A divide the vacuum passage way within casing tube 8 and limit the effect of the vacuum in the region designated 106A (shown in FIGS. 6 and 7) allowing the vacuum to act primarily in the region designated 102A. A single divider extending between the sides of the casing tube 8 could also be used.

Several different types of nozzle 11 for shaping fluid provided through fluid supply tube 10 are shown in FIGS. 9A and 9B and FIGS. 10A–10D. When the cutter 26 of the invention is operated, a high pressure fluid is supplied to the nozzle 11 through fluid supply tube 10. Each nozzle 11 has a cap 14 having one of several arrangements of fluid jet orifices 15. The fluid jet orifice 15 may be a single opening, as in FIG. 9A and 10B, or a plurality of openings, such as the three circular orifices 15 in FIG. 10A and five orifices 15 in FIG. 10C. Alternatively, a rectangular or beveled orifice 15 could be used, as in FIGS. 9B and 10D. Different fluid jet orifices 15 may be used to obtain more precise cutting, disintegration effect, or more rapid cutting.

Figure 11:
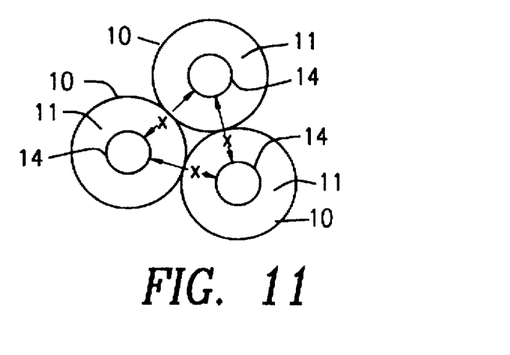
FIG. 11 is a bottom plan view of an arrangement of an embodiment of the cutter having multiple fluid jet nozzles.
Figure 12:
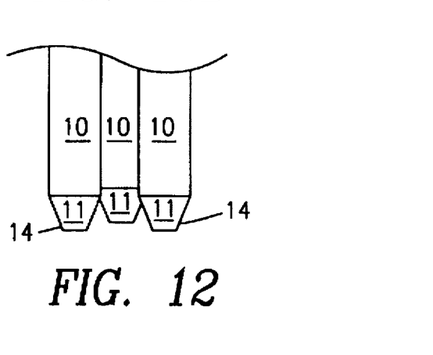
FIG. 12 is a side elevation of the arrangement of FIG. 11.

It is also envisioned that two or more fluid supply tubes 10 could be used within the cutter 26, to provide multiple fluid jets through nozzles 11, as shown in FIGS. 11 and 12. Any of the orifices shown in FIGS. 9A, 9B, and 10A–10D could be used in caps 14. A combination of fluid jet orifices 15 could be used also, instead of matching the type of orifice 15 and cap 14 used on each nozzle 11.

When the cutter has either multiple orifices 15 or multiple fluid supply tubes 10, a gap designated X in FIG. 11 must be present between each adjacent pair of orifices 15 or nozzles 11. This prevents the fluid jets from effectively occluding orifice 7 and aspiration port 12, and allows the low vacuum suction to be effective at orifice 7 where the low vacuum can aspirate the tissue to be cut through orifice 7.

Figure 13A:
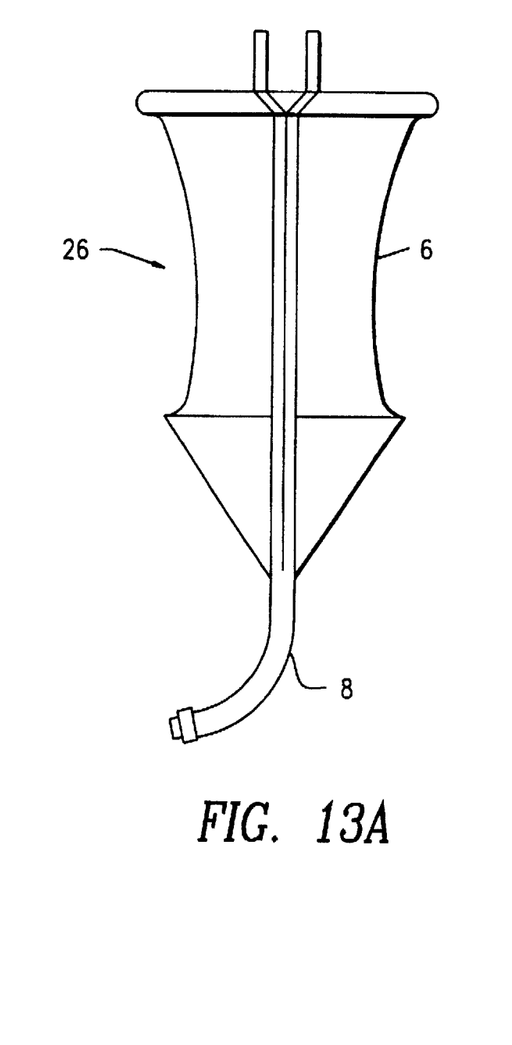
FIGS. 13A–13B are front elevations of alternate embodiments of the shape of the casing tube of a cutter of the present invention.
Figure 13B:
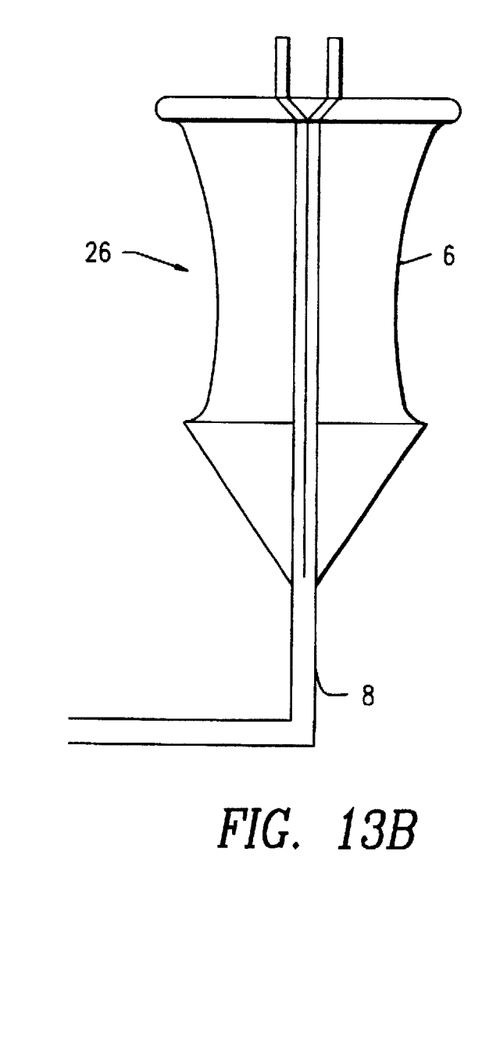

In FIGS. 13A and 13B, alternate shapes for the outer casing 8 of a handpiece 26 of the invention are disclosed. The nature of the fluid jet cutter allows the shape of the outer casing 8 to be different. As long as the vacuum passages 100, 102, 102a and fluid jet tube 10 remain unrestricted, the outer casing can be shaped to suit the particular needs of any surgery.

Figure 14:
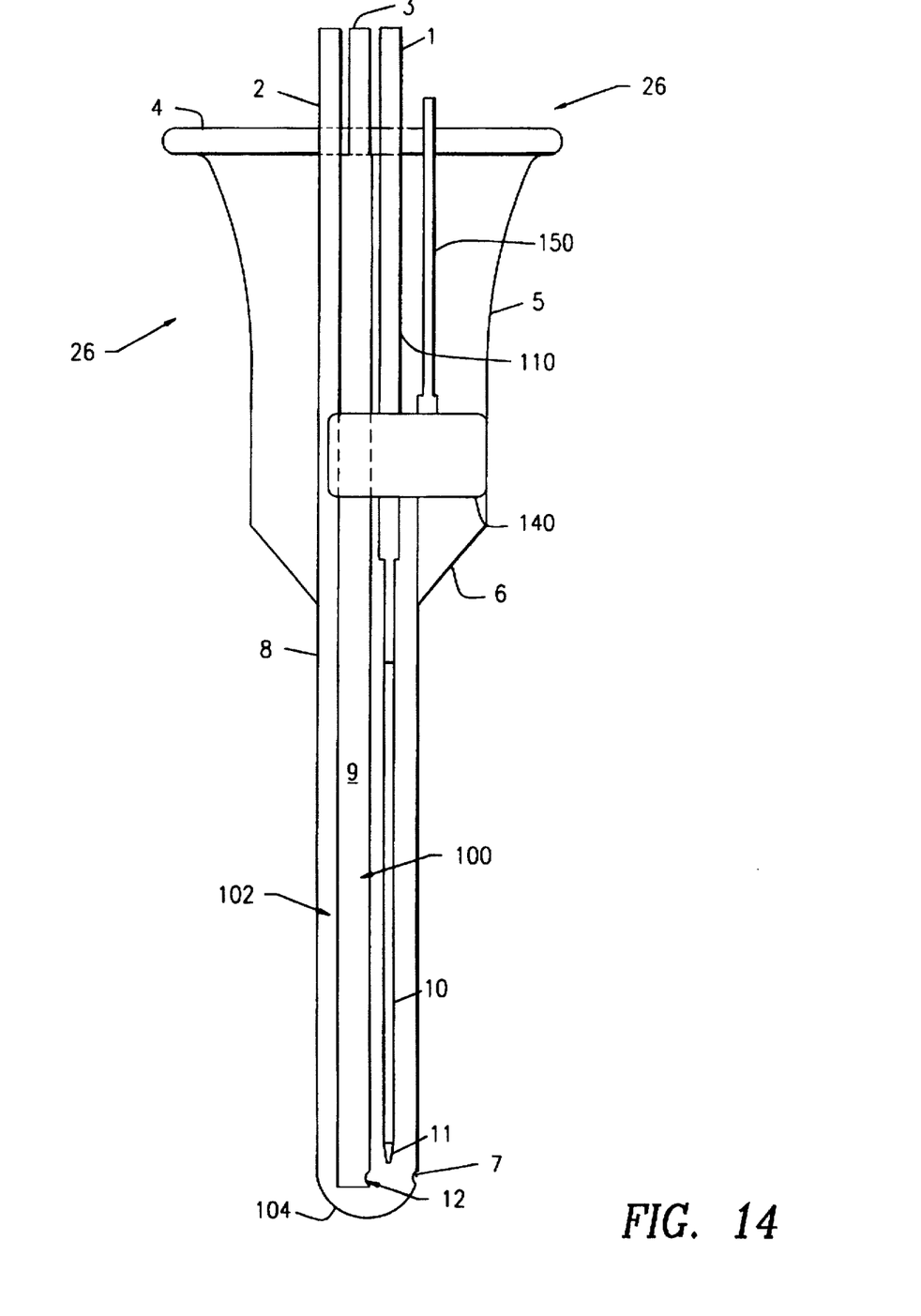
FIG. 14 is a sectional view of the cutter tip of yet another embodiment of the cutter handpiece.

Another embodiment of the cutter is shown in FIGS. 14–17, which has a rotating fluid supply tube 10 to further enhance the cutting action of the fluid jet. As shown in FIG. 14 a casing 140 containing a motor or pump which can be used to either rotate fluid supply tube 10 about its long axis or to cause the fluid jet to rotate is located inside hand piece 5. An electrical or mechanical connector 150 can be used to provide power or mode of force to a pump or motor within casing 140. Fluid supply port 1 is connected to upper fluid supply tube 110 which enters casing 140 and is sealedly connected to the casing. Fluid supply tube 10 is connected to the opposite side of casing 140 and may be either rotatably or securely connected to casing 140 as needed. In this embodiment, either the fluid supply tube 10 or the fluid contained within the fluid supply tube 10 may be rotated to enhance the cutting action of the water jet.

Figures 15, 16, 17:
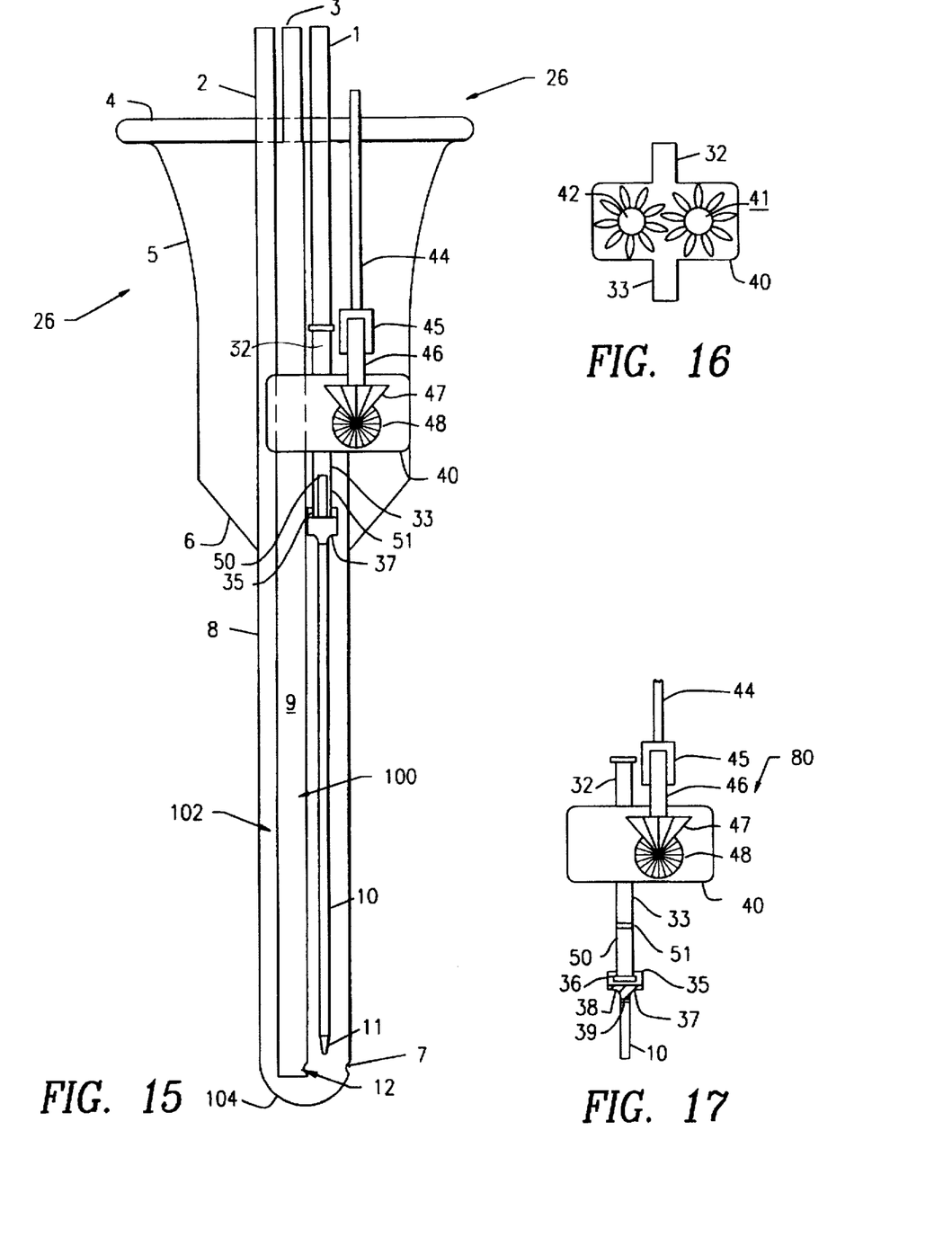
FIG. 15 is a sectional view of a further embodiment of the cutter handpiece.
FIG. 16 is a sectional view of a pump for use inside the embodiment of the cutter handpiece of the invention shown in FIG. 15.
FIG. 17 is a sectional view of a pump and turbine-driven rotating fluid jet supply tube for use with the cutter handpiece shown in FIG. 15.

FIGS. 15–17 show one embodiment for rotating the fluid supply tube 10. An internal pump 80 is located within the grip 5 which is connected to a hollow shaft 50 having a rotatable connection with a turbine 37 which is rigidly connected via an O-ring seal 39 to fluid supply tube 10.

The internal pump 80 has a fluid input 32 and a fluid output 33 connected to opposite sides of a pump casing 40. Inside the pump casing 40, are two interconnected driven gears 41, 42. A driven beveled gear 48 is connected to one of the driven gears 41, 42, and is in turn driven by a driving beveled gear 47, having shaft 46. Shaft 46 is connected to driving rod 44 by a clamp 45 or other known connecting means to prevent slipping during rotation of the rod 44 and shaft 46. The driving rod 44 can be coated to protect it, if desired, and may be connected to any known motive force, which may be generated in an attached console unit (not shown in FIGS. 15–17), for imparting a rotational movement to the rod 44. Alternatively, gear 48 may be driven by any known means within the cutter itself, such as an electric motor.

The fluid supplied through fluid supply port 1 enters the pump 80 through pump inlet 32 and is accelerated and pressurized through the pump casing 40 by the rotation of driven gears 41, 42. The driven gears 41, 42 are caused to rotate by the translation of the rotational movement of the driving rod 44 by beveled gears 47, 48, to which one of the driven gears is connected. The fluid exits pump 80 at pump outlet 33 under increased pressure and at higher velocity.

The pressurized fluid stream then passes into hollow shaft 50, which is connected at one end to pump outlet 33 by a second O-ring seal 51. Hollow shaft 50 has a bearing ring 36 at the other end located inside a bearing housing 35. Bearing housing 35 is freely rotatable around bearing ring 36, and is rigidly connected to turbine 37. Hollow shaft 50 communicates with turbine 37, and the pressurized fluid can pass from the hollow shaft 50 into the turbine 37, where it interacts with turbine blades 38 which are oriented such that the turbine 37 and bearing housing 35 are caused to rotate.

The turbine is rigidly connected to the proximal end of fluid supply tube 10 opposite the nozzle 11 by O-ring seal 39. The rigid connection forces fluid supply tube 10 to rotate when turbine 37 and housing 35 rotate. The pressurized fluid leaves turbine 37 and enters fluid supply tube 10, where it continues to nozzle 11, and is formed into a fluid jet, or several jets. The rotational motion of fluid supply tube 10 causes nozzle 11 to rotate also. When multiple orifices 15 in nozzle 11 or multiple fluid tubes and nozzles are used, the rotation results in spiral, or helical fluid jets being emitted from the nozzle 11.

The internal pump 80, or the bearing housing 35 and turbine 37 may be used alone, or in combination with each other, or other elements of the invention as disclosed. For instance, the fluid pressure may be increased prior to entering the fluid supply port 1 to accommodate the energy lost by operating the turbine 37 to rotate the fluid supply tube 10.

Figure 18:
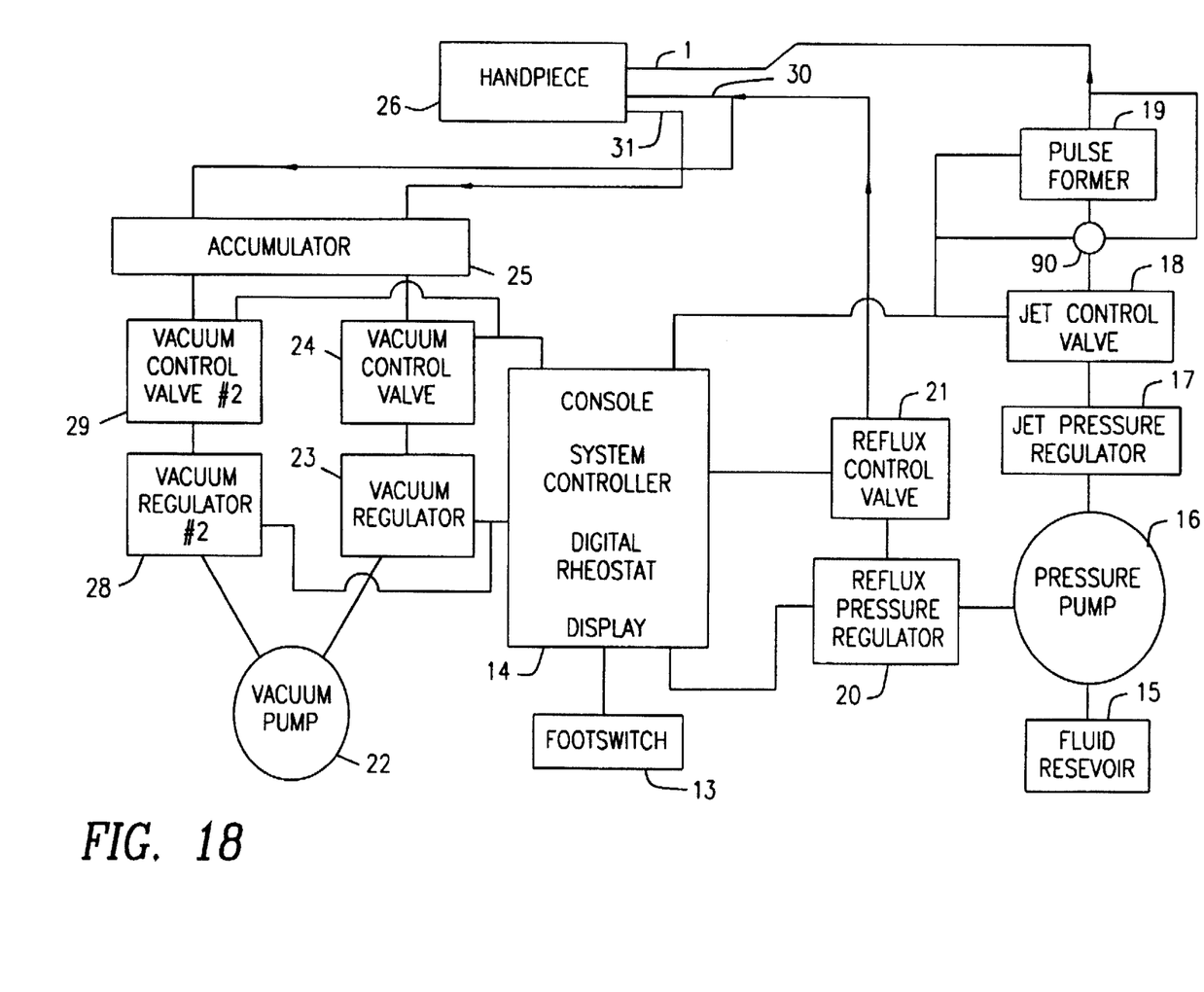
FIG. 18 is a schematic diagram of a control system for use with a cutter of the present invention.

A control console for use with the cutter of the invention is shown in FIG. 18. The console has a display means, logic board and software controller 14, vacuum means, pressurization means, a waste receptacle 25, reflux means, a pulse former 19, and a foot control switch 13 to allow a physician to use both hands for the surgical procedure.

A vacuum pump 22 has at least one vacuum regulator 23 and vacuum control valve 24 in series connected to the controller 14. Preferably, a second vacuum regulator 28 and second vacuum control valve 29 are connected to the vacuum pump to separately control a second vacuum level when a handpiece 26 having high and low vacuum passages 102, 100 is used. Each vacuum control valve 24, 29 is connected to an accumulator 25, for storing waste material from the cutter 26. The accumulator 25 may be sectioned or divided to prevent a loss of vacuum strength between the two vacuum systems. Separate vacuum lines 30, 31 connect the accumulator to the appropriate port on a handpiece 26 of the invention. Vacuum regulators and control valves may be controlled from controller panel 14.

The fluid supply for the fluid jet is pumped from a fluid reservoir 15 by pressure pump 16 to jet pressure regulator 17, through jet control valve 18, and optionally, through pulse former 19, to the fluid supply port 1. The controller 14 is used to set switch 90 to cause the pressurized fluid to flow to the pulse former 19 first or directly to the fluid supply port 1. Pulse former and jet control valve are controlled from the controller 14. Pressure pump 16 may be a piston type pump or any other known type of positive displacement pump. Pulse former 19 may be a solenoid which can rapidly hold and release the fluid supply to the cutter 26. Flexible high pressure tubing may also be used to connect each of the components to each other and to hand piece 26.

A reflux pressure regulator 20 is controlled by the controller 14 and connected to pressure pump 16. Reflux control valve 21 is also controlled by the controller 14 and connected between the low vacuum supply 30 and the reflux pressure regulator 20. When the reflux control valve 21 is operated by foot switch 13 a small quantity of low pressure fluid is delivered via flexible tubing 30 to chamber 100 in hand piece 26. Simultaneously, the water jet supply and vacuum systems are deactivated. This reflux system serves to safely dislodge any pieces of tissue which have become stuck in either orifice 7 or 12 and are blocking the orifices 7, 12 and inhibiting the cutting effectiveness of the cutter 26.

When used with the single vacuum embodiment of the cutter 26, the reflux system may be connected to the first vacuum port 2a via tubing 30.

It should be understood that although the term fluid has been used to describe the fluid used in the fluid jet cutter, it is intended that any physiological sterile fluid which is acceptable for use within the human body during surgical procedures can be used as the fluid in the cutting jet with this device.

Materials which are suitable for use with this invention include stainless steel, approximately 20 gauge in diameter or a synthetic polymer of similar strength, for the outer casing tube 8. The fluid supply tube 10 can also be made of stainless steel of a smaller gauge than the casing tube 8. Additionally, if the diameter of the fluid supply tube 10 is sufficiently small, the nozzle 11 may be eliminated and the fluid jet may be formed solely by the water supply tube 10. Alternatively, the nozzle 11 may be formed in a unitary construction with the fluid supply tube 10. Flexible tubing used to connect various components of the control system to the hand piece 26 and to supply fluid to the hand piece 26 may be made of flexible metal, PVC, polycarbonate, or any other material of suitable strength to withstand the pressures produced. The nozzle cap 14 may be formed from metal or from a sapphire or other suitable material, and the outlet orifices 15 may be drilled using, for instance, conventional laser technology. The size of the fluid jets formed by the nozzle 11 should range from 5 to 150 microns, and the pressurized fluid should be maintained near 1,000 psi in order to ensure that the fluid jet is sufficiently strong to cut tissues. The vacuum strength present at the opening 7 can be variable controlled, but may be in the range of 3–5 psi, for vitrectomy surgery, and possibly higher for other types of surgery.

While a specific embodiment of the invention has been shown and described in detail to illustrate the application of the principles of the invention, it will be understood that the invention may be embodied otherwise without departing from such principles.

What is claimed is:

1. A microsurgical vitrectomy fluid jet cutting device for cutting and removing vitreous from an eye, comprising:
    a substantially rigid casing tube defining a chamber;
    the casing tube having a first vacuum port communicating with the chamber proximate a first end of the tube and an opening through the tube proximate a second end;
    vacuum means for applying a vacuum to the chamber through the first vacuum port to draw the vitreous into the chamber through the opening;
    a fluid jet supply tube extending in the casing tube and having a discharge located within the chamber adjacent the opening oriented to discharge a fluid jet across a path through which the vitreous is drawn, whereby a fluid jet discharged through the discharge cuts the vitreous drawn through the opening and the cut vitreous is drawn from the chamber through the vacuum port; and a hand grip connected to the casing tube for concurrently manipulating the hand grip and the casing tube.

2. A microsurgical fluid jet cutting device according to claim 1, further comprising control means for controlling and monitoring the vacuum means and the fluid jet discharge.

3. A microsurgical fluid jet cutting device according to claim 2, further comprising pressurizing means for pressurizing the fluid jet discharged from the discharge operatively connected to the fluid jet supply at one of outside the casing tube and inside the chamber.

4. A microsurgical fluid jet cutting device according to claim 3, wherein the discharge comprises at least one nozzle connected to the fluid jet supply tube, the nozzle having at least one outlet positioned adjacent the opening.

5. A microsurgical fluid jet cutting device according to claim 3, wherein the pressurizing means comprises a positive displacement pump.

6. A microsurgical fluid jet cutting device according to claim 5, wherein the positive displacement pump is located between the casing tube and the fluid supply tube.

7. A microsurgical fluid jet cutting device according to claim 1, further comprising a closed vacuum tube housing a low vacuum chamber therein; a second vacuum port extending through the casing tube and the vacuum tube proximate the first end; an aspiration orifice through the vacuum tube aligned with the opening in the outer casing; and second vacuum means connected to the second vacuum port for providing a second vacuum at the aspiration orifice in the vacuum tube, whereby the second vacuum draws the vitreous into the chamber through the opening and aspirates tissue cut by the fluid jet discharge, the excess fluid jet discharge being drawn from the chamber by the first vacuum through the first vacuum port.

8. A microsurgical fluid jet cutting device according to claim 7, further comprising control means for controlling and monitoring each of the first and second vacuum means and the fluid jet discharge.

9. A microsurgical fluid jet cutting device according to claim 8, wherein the control means further comprises means for pulsing the fluid jet.

10. A microsurgical fluid jet cutting device according to claim 7, wherein the first and second vacuum means comprise a common vacuum source; a pair of vacuum regulators, each connected to the common vacuum source and controlled by the control means for setting a vacuum strength, each vacuum regulator connected to one of a pair of vacuum control valves, each vacuum control valve controlled by the control means; a waste storage receptacle, connected between each vacuum control valve and each of the first and second vacuum ports; a reflux wash means for providing a pressurized fluid wash; a reflux control valve connected between the second vacuum port and the reflux wash means and controlled by the control means.

11. A microsurgical fluid jet cutting device according to claim 7, wherein the casing tube is shaped having one of an arcuate segment end and a right angle bend.

12. A microsurgical fluid jet cutting device according to claim 7, further comprising at least one divider located within the casing tube, each divider extending from the first end toward the second end, and connected between a side of the casing tube and one of a second side of the casing tube, the fluid jet supply tube, and the vacuum tube.

13. A microsurgical fluid jet cutting device according to claim 7, further comprising rotary means for rotating the fluid jet supply tube within the casing tube.

14. A microsurgical fluid jet cutting device according to claim 13, wherein the rotary means comprises a hollow shaft connected to the fluid jet supply tube; a bearing ring at a bearing end of the hollow shaft; a bearing housing rotatably connected around the bearing ring; a turbine rigidly connected to the bearing housing, the bearing end of the hollow shaft in communication with the turbine, the turbine having a turbine outlet rigidly connected to the fluid jet supply tube, such that when pressurized fluid is supplied through the fluid supply port to the hollow shaft, that the pressurized fluid enters the turbine and causes the turbine to rotate about the bearing ring before passing through the turbine outlet to the fluid supply tube.

15. A microsurgical fluid jet cutting device according to claim 7, wherein the discharge comprises at least one nozzle connected to the fluid jet supply tube, the nozzle having at least one outlet positioned adjacent the opening.

16. A microsurgical fluid jet cutting device according to claim 7, further comprising pressurizing means for pressurizing the fluid jet discharged from the discharge operatively connected to the fluid jet supply at one of outside the casing tube and inside the chamber.

17. A microsurgical fluid jet cutting device according to claim 16, wherein the pressurizing means comprises a positive displacement pump.

18. A microsurgical fluid jet cutting device according to claim 17, wherein the positive displacement pump is located between the casing tube and the fluid supply tube.

19. A microsurgical fluid jet cutting device according to claim 1, further comprising rotary means for rotating the fluid jet supply tube within the casing tube when the fluid jet is present.

20. A microsurgical fluid jet cutting device according to claim 19, wherein the rotary means comprises a hollow shaft connected to the fluid jet supply tube; a bearing ring at a bearing end of the hollow shaft; a bearing housing rotatably connected around the bearing ring; a turbine rigidly connected to the bearing housing, the bearing end of the hollow shaft in communication with the turbine, the turbine having a turbine outlet rigidly connected to the fluid jet supply tube, such that when pressurized fluid is supplied through the fluid supply port to the hollow shaft, that the pressurized fluid enters the turbine and causes the turbine to rotate about the bearing ring before passing through the turbine outlet to the fluid jet supply tube.

21. A microsurgical fluid jet cutting device according to claim 1, further comprising at least one planar located within the casing tube, the planar extending from the first end toward the second end, and connected between a side of the casing tube and one of a second side of the casing tube and the fluid jet supply tube.

22. A microsurgical fluid jet cutting device according to claim 1, further comprising pulsing means for pulsing the fluid jet discharge.

23. A microsurgical fluid jet cutting device according to claim 1, further comprising control means for controlling and monitoring the vacuum means and fluid jet, wherein the first vacuum means comprises a vacuum source; a vacuum regulator connected to the vacuum source and controlled by the control means for setting a vacuum strength, the vacuum regulator connected to a vacuum control valve controlled by the control means; a waste storage receptacle, connected between the vacuum control valve and the first vacuum port; a reflux wash means for providing a pressurized fluid wash; a reflux control valve connected between the first vacuum port and the reflux wash means and controlled by the control means.

24. A microsurgical fluid jet cutting device according to claim 1, wherein the casing tube is shaped having one of an arcuate segment end and a right angle bend.

25. A method for performing a surgery on a patient's tissues, using a microsurgical fluid jet cutter having a fluid jet provided within a casing, the fluid jet positioned adjacent an orifice in the casing, and vacuum means for producing a vacuum within the casing for drawing material through the orifice into the path of the fluid jet within the casing, the method comprising:

inserting the casing within a patient's body;

positioning the casing orifice adjacent a tissue in the patient's body;

activating the fluid jet cutter, such that a fluid jet is produced and the vacuum means forms a vacuum inside the casing;

vacuum suctioning a portion of the tissue through the orifice in the casing with the vacuum means;

emulsifying the tissue with the fluid jet inside the casing;

aspirating the emulsified tissue and fluid from the fluid jet through the casing with the vacuum means;

repeating the vacuum suctioning, emulsifying and aspirating until all of the tissue has been removed; and removing the casing from the patient's body.

26. A method according to claim 25, further comprising pulsing the fluid jet with pulsing means for providing the fluid jet in a series of discontinuous pulses.

27. A method according to claim 25, further comprising regulating the vacuum means and fluid jet with a control means for regulating the vacuum provided by the vacuum means and the fluid jet to prevent emulsified tissue and fluid from exiting the casing through the orifice.

28. A method for performing a vitrectomy surgery on a patient's eye, using a microsurgical fluid jet cutter having a fluid jet provided within a casing, the fluid jet positioned adjacent an orifice in the casing, and vacuum means for producing a vacuum within the casing for drawing material through the orifice into the path of the fluid jet within the casing, the method comprising:

inserting the casing within a patient's eye;

positioning the casing orifice adjacent vitreous in the patient's eye;

activating the fluid jet cutter, such that a fluid jet is produced and the vacuum means forms a vacuum inside the casing;

vacuum suctioning a portion of the vitreous through the orifice in the casing with the vacuum means;

emulsifying the vitreous with the fluid jet inside the casing;

aspirating the emulsified vitreous and fluid from the fluid jet through the casing with the vacuum means;

repeating the vacuum suctioning, emulsifying and aspirating until all of the vitreous has been removed; and removing the casing from the patient's eye.

29. A method according to claim 28, further comprising pulsing the fluid jet with pulsing means for providing the fluid jet in a series of discontinuous pulses.

30. A method according to claim 28, further comprising regulating the vacuum means and fluid jet with a control means for regulating the vacuum provided by the vacuum means and the fluid jet to prevent emulsified vitreous and fluid from exiting the casing through the orifice.

31. A microsurgical fluid jet cutting device for cutting and removing tissue, comprising:

a casing tube defining a chamber;

the casing tube having a first vacuum port communicating with the chamber and proximate a first end of the tube and an opening through the tube proximate a second end;

vacuum means for applying a vacuum to the chamber through the first vacuum port to draw the tissue into the chamber through the opening;

a fluid jet supply tube extending in the casing tube and having a discharge located within the chamber;

a vacuum tube housing a low vacuum chamber therein;

a second vacuum port extending through the casing tube and the vacuum tube proximate the first end;

an aspiration orifice through the vacuum tube; and second vacuum means connected to the second vacuum port for providing a second vacuum at the aspiration orifice in the vacuum tube, so that when a fluid jet discharged through the discharge is adjacent the opening, the fluid jet cuts tissue drawn through the opening into the chamber by the second vacuum, which aspirates tissue cut by the fluid jet discharge, the excess fluid jet discharge being drawn from the chamber by the first vacuum through the first vacuum port.

32. A microsurgical fluid jet cutting device according to claim 31, further comprising control means for controlling and monitoring each of the first and second vacuum means and the fluid jet discharge.

33. A microsurgical fluid jet cutting device according to claim 32, wherein the control means further comprises means for pulsing the fluid jet.

34. A microsurgical fluid jet cutting device according to claim 31, wherein the first and second vacuum means comprise a common vacuum source; a pair of vacuum regulators, each connected to the common vacuum source and controlled by the control means for setting a vacuum strength, each vacuum regulator connected to one of a pair of vacuum control valves, each vacuum control valve controlled by the control means; a waste storage receptacle, connected between each vacuum control valve and each of the first and second vacuum ports; a reflux wash means for providing a pressurized fluid wash; a reflux control valve connected between the second vacuum port and the reflux wash means and controlled by the control means.

35. A microsurgical fluid jet cutting device according to claim 31, wherein the casing tube is shaped having one of an arcuate segment end and a right angle bend.

36. A microsurgical fluid jet cutting device according to claim 31, further comprising at least one divider located within the casing tube, each divider extending from the first end toward the second end, and connected between a side of the casing tube and one of a second side of the casing tube, the fluid jet supply tube, and the vacuum tube.

37. A microsurgical fluid jet cutting device according to claim 31, further comprising rotary means for rotating the fluid jet supply tube within the casing tube.

38. A microsurgical fluid jet cutting device according to claim 37, wherein the rotary means comprises a hollow shaft connected to the fluid jet supply tube; a bearing ring at a bearing end of the hollow shaft; a bearing housing rotatably connected around the bearing ring; a turbine rigidly connected to the bearing housing, the bearing end of the hollow shaft in communication with the turbine, the turbine having a turbine outlet rigidly connected to the fluid jet supply tube, such that when pressurized fluid is supplied through the fluid supply port to the hollow shaft, that the pressurized fluid enters the turbine and causes the turbine to rotate about the bearing ring before passing through the turbine outlet to the fluid supply tube.

39. A microsurgical fluid jet cutting device according to claim 31, wherein the discharge comprises at least one nozzle connected to the fluid jet supply tube, the nozzle having at least one outlet positioned adjacent the opening.

40. A microsurgical fluid jet cutting device according to claim 39, wherein the at least one outlet comprises three outlets arranged in a triangular pattern.

41. A microsurgical fluid jet cutting device according to claim 39, wherein the at least one outlet comprises five outlets arranged in a cross pattern.

42. A microsurgical fluid jet cutting device according to claim 39, wherein the at least one outlet comprises three rectangular outlets, two of the three rectangular outlets being horizontally spaced apart and vertically aligned.

43. A microsurgical fluid jet cutting device according to claim 39, wherein the at least one outlet comprises one outlet formed as a slot oriented obliquely to a nozzle longitudinal axis.

44. A microsurgical fluid jet cutting device according to claim 31, further comprising pressurizing means for pressurizing the fluid jet discharged from the discharge operatively connected to the fluid jet supply at one of outside the casing tube and inside the chamber.

45. A microsurgical fluid jet cutting device according to claim 44, wherein the pressurizing means comprises a positive displacement pump.

46. A microsurgical fluid jet cutting device according to claim 45, wherein the positive displacement pump is located between the casing tube and the fluid supply tube.

47. A microsurgical fluid jet cutting device for cutting and removing tissue, comprising:

a casing tube defining a chamber;

the casing tube having a first vacuum port communicating with the chamber and proximate a first end of the tube and an opening through the tube proximate a second end;

vacuum means for applying a vacuum to the chamber through the first vacuum port to draw the tissue into the chamber through the opening;

a fluid jet supply tube extending in the casing tube and having a discharge located within the chamber;

rotary means for rotating the fluid jet supply tube within the casing tube, the rotary means comprising, a hollow shaft connected to the fluid jet supply tube; a bearing ring at a bearing end of the hollow shaft; a bearing housing rotatably connected around the bearing ring; a turbine rigidly connected to the bearing housing, the bearing end of the hollow shaft in communication with the turbine, the turbine having a turbine outlet rigidly connected to the fluid jet supply tube, such that when pressurized fluid is supplied through the fluid supply port to the hollow shaft, that the pressurized fluid enters the turbine and causes the turbine to rotate about the bearing ring before passing through the turbine outlet to the fluid jet supply tube, whereby a fluid jet discharged through the discharge is adjacent the opening and the fluid jet cuts the tissue drawn through the opening and the cut tissue is drawn from the chamber through the first vacuum port.

48. A method for performing a surgery on a patient's tissues, using a microsurgical fluid jet cutter having a fluid jet provided within a casing, the fluid jet positioned adjacent an orifice in the casing, and suction means for producing a vacuum within the casing for drawing material through the orifice into the path of the fluid jet within the casing, the method comprising:

inserting the casing within a patient's body;

positioning the casing orifice adjacent a tissue in the patient's body;

activating the fluid jet cutter, such that a fluid jet is produced and the suction means forms a vacuum inside the casing;

rotating the fluid jet within the casing;

suctioning a portion of the tissue through the orifice in the casing with the suction means;

emulsifying the tissue with the fluid jet inside the casing;

aspirating the emulisified tissue and fluid from the fluid jet through the casing with the vacuum means;

repeating the suctioning, emulsifying and aspirating until all of the tissue has been removed; and removing the casing from the patient's body.

49. A method for performing a vitrectomy surgery on a patient's eye, using a microsurgical fluid jet cutter having a fluid jet provided within a casing, the fluid jet positioned adjacent an orifice in the casing, and suction means for producing a vacuum within the casing for drawing material through the orifice into the path of the fluid jet within the casing, the method comprising:

inserting the casing within a patient's eye;

positioning the casing orifice adjacent vitreous in the patient's eye;

activating the fluid jet cutter, such that a fluid jet is produced and the suction means forms a vacuum inside the casing;

rotating the fluid jet within the casing;

suctioning a portion of the vitreous through the orifice in the casing with the suction means;

emulsifying the vitreous with the fluid jet inside the casing;

aspirating the emulisified vitreous and fluid from the fluid jet through the casing with the vacuum means;

repeating the suctioning, emulsifying and aspirating until all of the vitreous has been removed; and removing the casing from the patient's eye.

* * * * *